(12) United States Patent
Leigh

(10) Patent No.: US 11,617,893 B2
(45) Date of Patent: Apr. 4, 2023

(54) EXTERNAL SYSTEM FOR IMPLANTED MEDICAL DEVICES

(71) Applicant: COCHLEAR LIMITED, Macquarie University (AU)

(72) Inventor: Charles Roger Leigh, Macquarie University (AU)

(73) Assignee: COCHLEAR LIMITED, Macquarie University (AU)

( * ) Notice: Subject to any disclaimer, the term of this patent is extended or adjusted under 35 U.S.C. 154(b) by 96 days.

(21) Appl. No.: 16/758,216

(22) PCT Filed: Oct. 22, 2018

(86) PCT No.: PCT/IB2018/001334
§ 371 (c)(1),
(2) Date: Apr. 22, 2020

(87) PCT Pub. No.: WO2019/081981
PCT Pub. Date: May 2, 2019

(65) Prior Publication Data
US 2020/0324127 A1 Oct. 15, 2020

Related U.S. Application Data

(60) Provisional application No. 62/576,217, filed on Oct. 24, 2017.

(51) Int. Cl.
*A61N 1/37* (2006.01)
*A61N 1/378* (2006.01)
(Continued)

(52) U.S. Cl.
CPC ....... *A61N 1/3787* (2013.01); *A61N 1/36038* (2017.08); *A61N 1/37223* (2013.01)

(58) Field of Classification Search
CPC .............. A61N 1/3787; A61N 1/36038; A61N 1/37223; A61N 1/36036; A61N 1/0541
See application file for complete search history.

(56) References Cited

U.S. PATENT DOCUMENTS 7,266,209 B1 * 9/2007 House ................ A61N 1/36038
381/331
10,525,271 B2 1/2020 Janssen et al.
(Continued)

FOREIGN PATENT DOCUMENTS

KR 10-2005-0039445 A 4/2005

OTHER PUBLICATIONS

International Search Report and Written Opinion of the International Searching Authority for International Patent Application No. PCT/IB2018/001334 dated Mar. 28, 2019, 11 pages.

*Primary Examiner* — Eric D. Bertram
(74) *Attorney, Agent, or Firm* — Edell, Shapiro & Finnan, LLC

(57) ABSTRACT

Technologies disclosed herein can be used to provide power and data to an implantable device implanted in a recipient, such as when the recipient is not wearing an external device. An example system includes a pillow or other headrest configured as a power and data source for an implanted medical device. Disclosed technologies can be configured to continuously provide power and data to an implantable medical devices over a period of time, such as substantially the entire period of time where the recipient is resting their head on the pillow.

20 Claims, 6 Drawing Sheets

(51) Int. Cl.
A61N 1/36 (2006.01)
A61N 1/372 (2006.01)

(56) References Cited

U.S. PATENT DOCUMENTS

| | | |
|---|---|---|
| 2009/0067653 A1 | 3/2009 | Meskens et al. |
| 2009/0082835 A1* | 3/2009 | Jaax .................. H02J 7/007192 607/61 |
| 2009/0216296 A1 | 8/2009 | Meskens |
| 2010/0076522 A1* | 3/2010 | Hennig .............. A61N 1/37252 607/60 |
| 2011/0046730 A1* | 2/2011 | Meskens ............ A61N 1/36038 607/55 |
| 2012/0041515 A1 | 2/2012 | Meskens |
| 2012/0053657 A1* | 3/2012 | Parker .................. A61N 1/3787 607/61 |
| 2014/0270212 A1* | 9/2014 | Ridler ...................... H04R 25/30 381/60 |
| 2015/0375003 A1* | 12/2015 | Meskens ................. H02J 50/40 607/57 |
| 2016/0126771 A1* | 5/2016 | Aghassian ............ A61N 1/3787 320/108 |
| 2016/0375243 A1 | 12/2016 | Roehrlein et al. |
| 2017/0127196 A1* | 5/2017 | Blum ...................... H02J 50/12 |
| 2017/0202467 A1* | 7/2017 | Zitnik .................. A61B 5/6877 |
| 2018/0241564 A1* | 8/2018 | Peterson ............ A61N 1/37254 |
| 2018/0262037 A1* | 9/2018 | Meskens ............... H02J 50/402 |
| 2018/0333584 A1* | 11/2018 | Meskens ................ H02J 50/12 |
| 2019/0054305 A1* | 2/2019 | Janssen ............... H04R 25/305 |
| 2019/0074585 A1* | 3/2019 | Vavelin .................... H01Q 7/00 |
| 2020/0254249 A1* | 8/2020 | Rondoni ............ A61N 1/36139 |

* cited by examiner

EXTERNAL SYSTEM FOR IMPLANTED MEDICAL DEVICES

This application is a National Stage Entry of PCT International Patent Application No. PCT/IB2018/001334, which was filed on Oct. 22, 2018, and which claims priority to U.S. Provisional Patent Application No. 62/576,217, which was filed Oct. 24, 2017. The entire disclosure of both of these applications is hereby incorporated by reference in its entirety.

BACKGROUND

Hearing loss, which can be due to many different causes, is generally of two types: conductive and sensorineural. In many people who are profoundly deaf, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate their auditory nerves in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem implants might also be proposed when a person experiences sensorineural hearing loss if the auditory nerve, which sends signals from the cochlear to the brain, is severed or not functional.

Conductive hearing loss occurs when the normal mechanical pathways that provide sound to hair cells in the cochlea are impeded, for example, by damage to the ossicular chain or the ear canal. Individuals suffering from conductive hearing loss can retain some form of residual hearing because some or all of the hair cells in the cochlea function normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and can be suitable for individuals who cannot derive sufficient benefit from conventional hearing aids.

SUMMARY

Technology disclosed herein includes systems, apparatuses, devices, and methods that facilitate functionality of implanted medical devices, such as auditory prostheses (e.g., cochlear implants). In an example, a coil is disposed in a pillow or other headrest and a processor causes the coil to provide power to an implanted medical device disposed proximate the coil. The coil-transmitted power can be the sole power source for the implanted medical device. The processor can further cause operational data to be provided to the implanted medical device, such as data representative of a sound environment in examples where the device is an auditory prosthesis.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Figure 1:
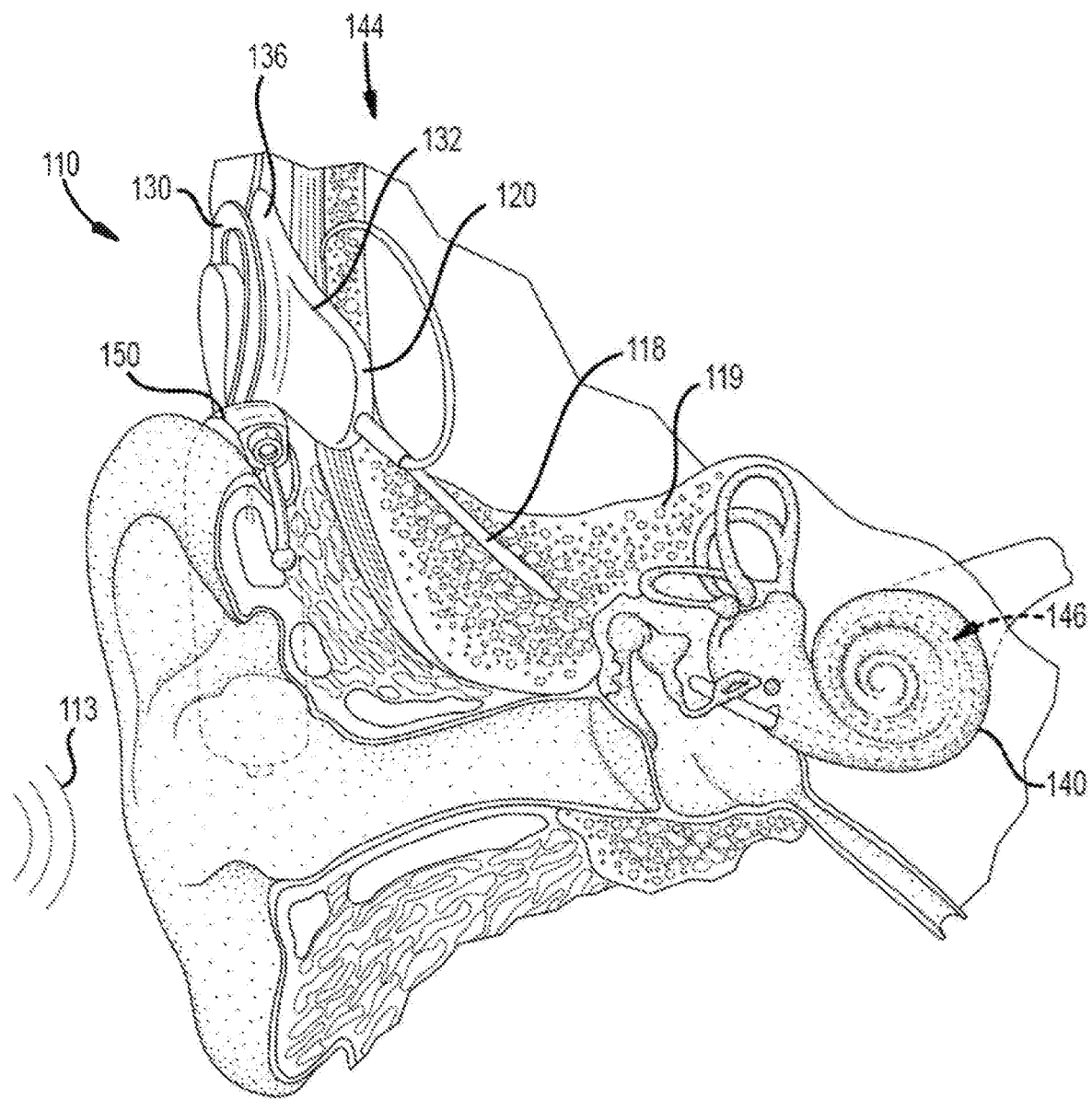
FIG. 1 illustrates an example cochlear implant system that includes an implantable component that can benefit from the use of a pillow system in accordance with examples of the technology.

The technologies described herein can be used with implanted medical devices, such as auditory prostheses (e.g., cochlear implants), that provide medical functions (e.g., providing pain management functionality or therapeutic electrical stimulation, such as deep brain stimulation). One variety of implanted devices depends on an external component to provide certain functionality. For example, the recipient of the implanted device can wear an external component that provides power and/or data (e.g., a signal representative of sound) to the implanted portion that allow the implanted device to function. In particular, the implanted device can lack a battery and can instead depend on an external power source providing continuous power for the implanted device to function. Although the external power source can continuously provide power, characteristics of the provided power need not be constant and may fluctuate. Additionally, where the implanted device is an auditory prosthesis such as a cochlear implant, the implanted device can lack its own sound input device (e.g., a microphone). It is sometimes desirable or necessary to remove the external component. For example, it is common for a recipient of an auditory prosthesis to remove an external portion of the prosthesis when going to sleep. Doing so can result in loss of function of the implanted portion of the prosthesis, which can make it impossible for recipient to hear ambient sound. This can be undesirable and can result in the recipient being unable to hear an alarm clock, a fire alarm, a knock at the door, a child crying and other important sounds. Loss of function would also prevent the implanted portion from responding to signals representative of streamed content (e.g., music streamed from a phone) or providing other functionality, such as providing tinnitus suppression noise.

The external component that provides power and/or data can be worn by a recipient of an auditory prosthesis. Advantageously, while a wearable external device is worn by a recipient, the external device is typically in very close proximity and tightly aligned with an implanted component. The wearable external device can be configured to operate in these conditions. By contrast, there are challenges in substituting a worn external device with an external device that is not configured to be worn. For example, an unworn device can generally be further away and less tightly aligned with the implanted component. This can create difficulties where the implanted device depends on an external device for power and data (e.g., where the implanted device lacks its own battery and microphone), and the external device can need to continuously and consistently provide power and data in order to allow for continuous and consistent functionality of the implanted device.

Technologies disclosed herein can be used to provide power and data to an implantable device in situations where a recipient is not wearing an external device. The technologies can overcome one or more challenges associated therewith. In an example, disclosed technologies can provide a source of power and/or data for an implanted medical device via a system that includes a pillow or other headrest. In such examples, some or all of the components of the external system are disposed in relation to the headrest. Disclosed technologies can be configured to continuously provide power and data to an implantable medical device over a period of time (e.g., substantially the entire period of time where the recipient is resting their head on the pillow). Characteristics of the continuously provided power need not be constant. For example, the power may fluctuate because the efficiency of the link between the implant and the pillow may vary as the recipient's head moves, causing the proximity of the coils to vary. The power to the implanted electronics can be smoothed for example using tank capacitors. It is common for recipients of an implanted medical device to remove their external devices while sleeping and during that time pillows are often placed in close proximity to the implanted prosthesis. In particular, auditory implants are typically disposed in close proximity to a recipients' ears and people typically place their head on a pillow such that one or both ears are close to the pillow. Thus, it can be beneficial to incorporate a pillow into a system for providing functionality of a worn external device while a recipient of an implantable device is sleeping. For a recipient of bilateral auditory implants, it may be sufficient for night time use for only one of the two devices to function. For instance, a first device being closest to the pillow may receive sufficient power and/or data to function while a second device that is further away from the pillow may receive insufficient power and/or data to function.

Pillows and other headrests are typically significantly larger than wearable external medical devices. This allows for the components of the disclosed system to have a larger size, which can help alleviate some drawbacks caused by the system not being worn. For example, the pillow can have a relatively larger area than a typical, wearable external device. The larger area allows the pillow to have comparatively more space in which to depose a coil (or other components) for transferring power and/or data to the implanted device. For example, the area enclosed by a pillow or headrest coil can be several times larger than the corresponding area for an implant coil. A larger size coil can allow for the pillow to transmit signals over a greater distance, should the medical device not be ideally positioned relative to the pillow. By incorporating one or more aspects of an external device in relation to a pillow, functionality of the implanted device can be maintained when a recipient removes a worn external device to rest on the pillow.

With reference to an example implantable auditory prosthesis, the prosthesis can depend on an external device for both power and data. Disclosed technologies can be configured to overcome challenges associated therewith. For example, an external pillow system can include data gathering functionality (e.g., via a sound input device, such a microphone), data processing functionality (e.g., a sound processor), data transmission functionality, and/or power transmission functionality (e.g., via interleaving power and data signals sent by a coil disposed within pillow). Disclosed technologies can be useful even where the implantable auditory prosthesis is not entirely dependent on an external device for power and/or data. For example, the implantable auditory prosthesis may include a battery but disclosed technologies may nonetheless provide operational power (e.g., obviating the need for the battery to provide power and drain itself,) and/or charging power to the implantable auditory prosthesis. For instance, the implantable component may be configured to use an external power source when one is present. As another example, disclosed technologies may provide data to the implantable auditory prosthesis even where the implantable auditory prosthesis is already receiving data from another source (e.g., an implanted or external sound input device). The data (e.g., data indicative of sound) may be mixed together and used by the implanted prosthesis.

Reference may be made herein to pillows or other headrests for concision, but disclosed technologies can be can be used in conjunction with a variety of articles. Headrests can include, for example, pillows, cushions, pads, head supports, and mattresses, among others. Such articles may be covered (e.g., with a pillow case) or uncovered. Additionally, the disclosed external system components can be used with any of a variety of systems in accordance with embodiments of the technology. For example, in many embodiments, the technology is used in conjunction with a conventional cochlear implant system. FIG. 1 depicts an example cochlear implant system that can benefit from use with technology disclosed herein.

FIG. 1 illustrates an example cochlear implant system 110 that includes an implantable component 144 typically having an internal receiver/transceiver unit 132, a stimulator unit 120, and an elongate lead 118. The internal receiver/transceiver unit 132 permits the cochlear implant system 110 to receive signals from and/or transmit signals to an external device 150. The external device 150 can be a button sound processor worn on the head that includes a receiver/transceiver coil 130 and sound processing components. Alternatively, the external device 150 can be just a transmitter/transceiver coil in communication with a behind-the-ear device that includes the sound processing components and microphone. Examples of pillow sound processor technology disclosed herein can function as the external device 150.

The implantable component 144 includes an internal coil 136, and preferably, a magnet (not shown) fixed relative to the internal coil 136. The magnet can be embedded in a pliable silicone or other biocompatible encapsulant, along with the internal coil 136. Signals sent generally correspond to external sound 113. The internal receiver/transceiver unit 132 and the stimulator unit 120 are hermetically sealed within a biocompatible housing, sometimes collectively referred to as a stimulator/receiver unit. Included magnets (not shown) can facilitate the operational alignment of an external coil 130 and the internal coil 136, enabling the internal coil 136 to receive power and stimulation data from the external coil 130. The external coil 130 is contained within an external portion. The elongate lead 118 has a proximal end connected to the stimulator unit 120, and a distal end 146 implanted in a cochlea 140 of the recipient. The elongate lead 118 extends from stimulator unit 120 to the cochlea 140 through a mastoid bone 119 of the recipient.

In certain examples, the external coil 130 transmits electrical signals (e.g., power and stimulation data) to the internal coil 136 via a radio frequency (RF) link. The internal coil 136 is typically a wire antenna coil having multiple turns of electrically insulated single-strand or multi-strand platinum or gold wire. The electrical insulation of the internal coil 136 can be provided by a flexible silicone molding. Various types of energy transfer, such as infrared (IR), electromagnetic, capacitive and inductive transfer, can be used to transfer the power and/or data from external device to cochlear implant. While the above description has described internal and external coils being formed from insulated wire, in many cases, the internal and/or external coils can be implemented via electrically conductive traces.

Figure 2:
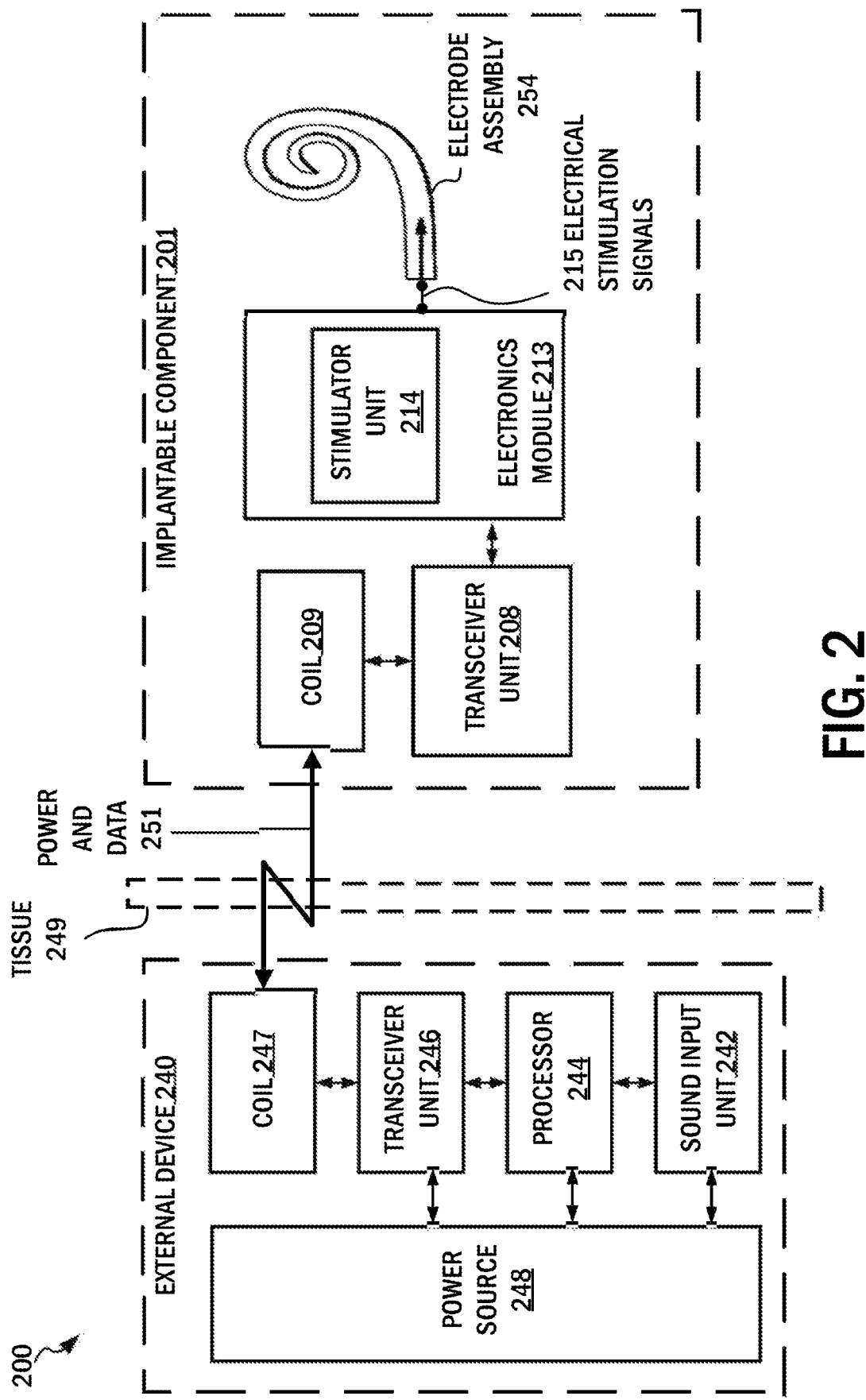
FIG. 2 is a functional block diagram of an example cochlear implant that can benefit from the use of a pillow system in accordance with examples of the technology.

FIG. 2 is a functional block diagram of a cochlear implant 200 that can benefit from the use of a pillow system in accordance with certain examples of the technology described herein. The cochlear implant 200 includes an implantable component 201 (e.g., implantable component 144 of FIG. 1) configured to be implanted beneath a recipient's skin or other tissue 249, and an external device 240 (e.g., the external device 150 of FIG. 1).

The external device 240 can be configured as a wearable external device, such that the external device 240 is worn by a recipient in close proximity to the implantable component, which can enable the implantable component 201 to receive power and stimulation data from the external device 240. As described in FIG. 1, magnets can be used to facilitate an operational alignment of the external device 240 with the implantable component 201. With the external device 240 and implantable component 201 in close proximity, the transfer of power and data can be accomplished through the use of near-field electromagnetic radiation, and the components of the external device 240 can be configured for use with near-field electromagnetic radiation.

Implantable component 201 can include a transceiver unit 208, electronics module 213, and an electrode assembly 254 (which can include an array of electrode contacts disposed on lead 118 of FIG. 1). The transceiver unit 208 is configured to transcutaneously receive power and/or data from external device 240. As used herein, transceiver unit 208 refers to any collection of one or more implanted components which form part of a transcutaneous energy transfer system. Further, transceiver unit 208 can include or be coupled to one or more components that receive and/or transmit data or power. For example, the illustrated example includes a coil 209 for a magnetic inductive arrangement coupled to the transceiver unit 208. Other arrangements are also possible, including an antenna for an alternative RF system, capacitive plates, or any other suitable arrangement. In an example, the data modulates the RF carrier or signal containing power. The transcutaneous communication link established by the transceiver unit 208 can use time interleaving of power and data on a single RF channel or band to transmit the power and data to the implantable component 201. In some examples, the processor 244 is configured to cause the transceiver unit 246 to interleave power and data signals, such as is described in U.S. Patent Application Publication No. 2009/0216296 to Meskens, which is incorporated herein by reference in its entirety for any and all purposes including for its description of techniques and devices for interleaving power and data. In this manner, the data signal is modulated with the power single, and a single coil can be used to transmit power and data to the implanted component 201. Various types of energy transfer, such as infrared (IR), electromagnetic, capacitive and inductive transfer, can be used to transfer the power and/or data from the external device 240 to the implantable component 201.

Aspects of the implantable component 201 require a source of power to provide functionality, such as receive signals, process data, or deliver electrical stimulation. The source of power that directly powers the operation of the aspects of the implantable component 201 can be described as operational power. There are two primary ways that the implantable component 201 can receive operational power: a power source internal to the implantable component 201 (e.g., a battery) or a power source external to the implantable component. However, other approaches or combinations of approaches are possible. For example, the implantable component may have a battery but nonetheless receive operational power from the external component (e.g., to preserve internal battery life when the battery is sufficiently charged).

The internal power source can be a power storage element (not pictured). The power storage element can be configured for the long-term storage of power, and can include, for example, one or more rechargeable batteries. Power can be received from an external source, such as the external device 240, and stored in the power storage element for long-term use (e.g., charge a battery of the power storage element). The power storage element can then provide power to the other components of the implantable component 201 over time as needed for operation without needing an external power source. In this manner, the power from the external source may be considered charging power rather than operational power because the power from the external power source is for charging the battery (which in turn provides operational power) rather than for directly powering aspects of the implantable component 201 that require power to operate. The power storage element can be a long-term power storage element configured to be a primary power source for the implantable component 201.

In many examples, the implantable component 201 receives operational power from the external device 240 and the implantable component 201 does not include an internal power source (e.g., a battery). In other words, the implantable component 201 is powered solely by the external device 240, which provides enough power to the implantable component 201 to allow the implantable component to operate (e.g., receive data signals and take an action in response). The operational power can directly power functionality of the device rather than charging a power storage element of the external device implantable component 201. In these examples, the implantable component 201 can include incidental components that can store a charge (e.g., capacitors) or small amounts of power, such as a small battery for keeping volatile memory powered or powering a clock (e.g., motherboard CMOS batteries). But such incidental components would not have enough power on their own to allow the implantable component to provide primary functionality of the implantable component 201 (e.g., receiving data signals and taking an action in response thereto, such as providing stimulation) and therefore cannot be said to provide operational power even if they are integral to the operation of the implantable component 201.

As shown, electronics module 213 includes a stimulator unit 214 (e.g., which can correspond to stimulator 120 of FIG. 1). Electronics module 213 can also include one or more other components used to generate or control delivery of electrical stimulation signals 215 to the recipient. As described above with respect to FIG. 1, a lead (e.g., elongate lead 118 of FIG. 1) can be inserted into the recipient's cochlea. The lead can include an electrode assembly 254 configured to deliver electrical stimulation signals 215 generated by the stimulator unit 214 to the cochlea.

In the example system 200 depicted in FIG. 2, the external device 240 includes a sound input unit 242, a sound processor 244, a transceiver unit 246, a coil 247, and a power source 248. The sound input unit 242 is a unit configured to receive sound input. The sound input unit 242 can be configured as a microphone (e.g., arranged to output audio data that is representative of a surrounding sound environment), an electrical input (e.g., a receiver for a frequency modulation (FM) hearing system), and/or another component for receiving sound input. The sound input unit 242 can be or include a mixer for mixing multiple sound inputs together.

The processor 244 is a processor configured to control one or more aspects of the system 200, including converting sound signals received from sound input unit 242 into data signals and causing the transceiver unit 246 to transmit power and/or data signals. The transceiver unit 246 can be configured to send or receive power and/or data 251. For example, the transceiver unit 246 can include circuit components that send power and data (e.g., inductively) via the coil 247. The data signals from the sound processor 244 can be transmitted, using the transceiver unit 246, to the implantable component 201 for use in providing stimulation or other medical functionality.

The transceiver unit 246 can include one or more antennas or coils for transmitting the power or data signal, such as coil 247. The coil 247 can be a wire antenna coil having of multiple turns of electrically insulated single-strand or multi-strand wire. The electrical insulation of the coil 247 can be provided by a flexible silicone molding. Various types of energy transfer, such as infrared (IR), radiofrequency (RF), electromagnetic, capacitive and inductive transfer, can be used to transfer the power and/or data from external device 240 to implantable component 201.

Figure 3:
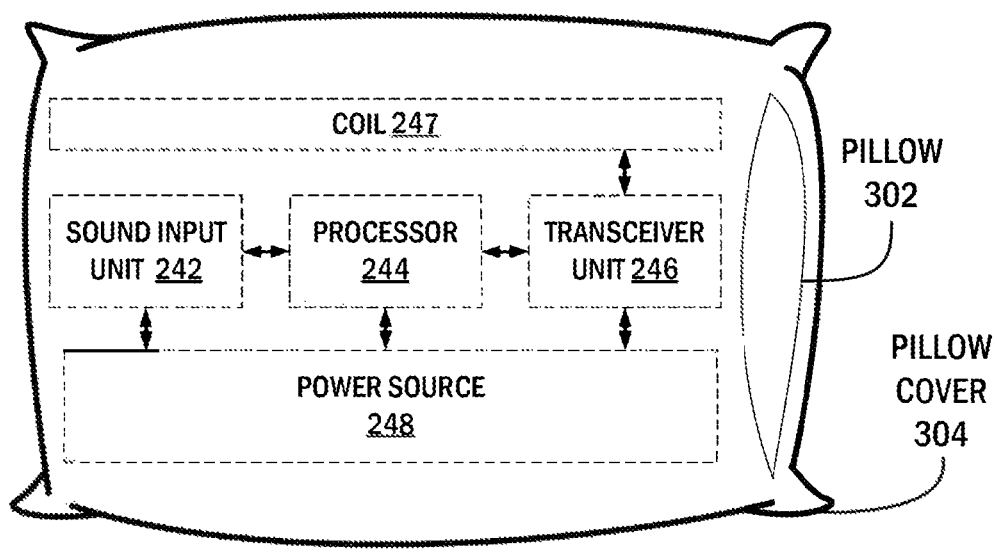
FIG. 3 illustrates an example pillow system for providing external device functionality for an implantable component.

FIG. 3 illustrates an example pillow system 300 for providing external device functionality for an implantable component. The system 300 can include components similar to external device 240 of FIG. 2, which includes components for sending power and/or data signals to an implantable device. The system 300 includes a pillow or headrest 302. The pillow 302 is an article on which a person can rest, such as while sleeping. The pillow 302 can include one or more aspects to provide or increase comfort, such as being made from a soft material. Disposed within the pillow 302 can be padding material, such as foam. The pillow 302 can be partially or fully enclosed by a pillow cover 304, which can be a removable covering for the pillow 302. The cover 304 can increase the comfort of the user by, for example, including padding that inhibits the ability of the user to feel the coil 247 or another component when resting on the pillow 302.

The system 300 can include components that provide functionality for an implantable component of a medical device. The components can be disposed within or coupled to the pillow 302. These components include a sound input unit 242, a processor 244, a transceiver unit 246, a coil 247, and a power source 248. The components can be configured to be used with the pillow 302. As illustrated, the components are disposed within the pillow 302 or the cover 304 overlaying the pillow, but they need not be. One or more of the components can be disposed outside of the pillow 302 and connected to the other components via a wired or wireless connection. For example, a sound input unit 242 such as a microphone can be disposed in a stand on a bedside table and communicatively coupled to the remaining components within the pillow. In further examples, components can be disposed even more remotely from the pillow 302 (e.g., placed in another room) but can nonetheless function as part of the system 300.

In an example, the system 300 is configured to be used while a recipient of an implantable component is resting on the pillow 302 and, in particular, while resting his or her head on the pillow 302. Compared to a wearable external device, the system 300 need not be worn by a recipient, and this difference can change how the system 300 is configured. For instance, a coil of a wearable external device is often disposed in close proximity at a known orientation to an implanted device. In such a configuration, the wearable external device would likely be configured to transmit data or power using near-field electromagnetic radiation. By contrast, the coil 247 (or other transmitter) of the system 300 would be no closer than the coil of a wearable external device, and in most cases would likely be disposed sufficiently far away as to provide power and data over some other type of transmission scheme, such as, far field electromagnetic radiation. The pillow system 300, and in particular the coil 247, can be configured to provide data and power using far field electromagnetic radiation. In some examples, near or far field may be used depending on a proximity detector. For instance, when a first proximity (e.g., a sufficiently short distance) to an implanted device is detected, near field electromagnetic radiation is used. When a second proximity (e.g., a sufficient far away distance) to an implanted device is detected, far field electromagnetic radiation is used.

The coil or antenna of the transceiver unit 246 can be sized or shaped to transmit or receive signals across a typical distance to an implanted device (e.g., implantable component 201) across various orientations of a recipient's head while resting on the pillow 302. For example, while typical external components for implantable medical devices are fixed (e.g., via a magnet) in a particular orientation in close proximity to the medical device, a recipient resting on the pillow 302 can be in a wider variety of orientations or configurations in relation to the coil 247. To overcome challenges associated with transmitting across this distance, the coil can be larger or otherwise configured to transmit across the wider variety of orientations than a typical, worn external device. In some examples, the coil or antenna can be integrated with a cover 304 of the pillow 302. This can allow the coil 247 to be closer to the recipient using the pillow 302 than if disposed inside the pillow 302. For example, the coil 247 can be sewn into, disposed within, attached to, coupled to, or otherwise integrated with the pillow cover 304. In some examples, the coil 247 can be positioned between the pillow 302 and the cover 304. In some examples there may be multiple coils distributed across the pillow surface with a system to select and use the coil with the best coupling to the implant.

The sound input unit 242 can be as described in to FIG. 2 and be configured for use as part of a pillow system. In some examples, the sound input unit 242 can be disposed within the pillow 302. In these examples, the sound input unit 242 can be configured to be resistant to being muffled by the material of the pillow 302 or the recipient's head. This can involve adjusting the frequency response of the sound input unit 242. In some examples, the sound input unit 242 is disposed outside of the pillow to alleviate the sound input being muffled or picking up unwanted noise from the recipient.

The processor 244 can be as described in relation to FIG. 2 and be configured for use as a part of a pillow sound processor. In examples where the processor 244 is disposed within the pillow 302, associated structures to dissipate heat from the processor 244 can be desirable. In an example, the processor 244 can be configured to be especially low-power to reduce the amount of heat generated by the processor 244 or can be especially tolerant of high temperatures. The processor can include a large heat sink or a heat dissipation configuration suited for the purpose. In some examples, the heat sink can be integrated into one or more of the comfort features of the pillow 302, such as the filling of the pillow 302. Where the pillow 302 includes a spring, the spring can also act as a heat sink. The transceiver unit 246 can be as described in relation to FIG. 2 and be configured for use as part of a pillow sound processor. As with the processor 244, the transceiver unit 246 can be disposed within or coupled to the pillow 302. These heat dissipation strategies can also be applied to other elements such as the coil.

The power source 248 can be as described in relation to FIG. 2 and be configured for use as part of a pillow system. The power source 248 can be a power storage unit (e.g., a battery) or be components for directly receiving power from an external source, such as a wall electrical outlet. In some examples, components of the system 300 can be powered or charged wirelessly, such as via a charging pad disposed proximate the pillow 302.

Figure 4:
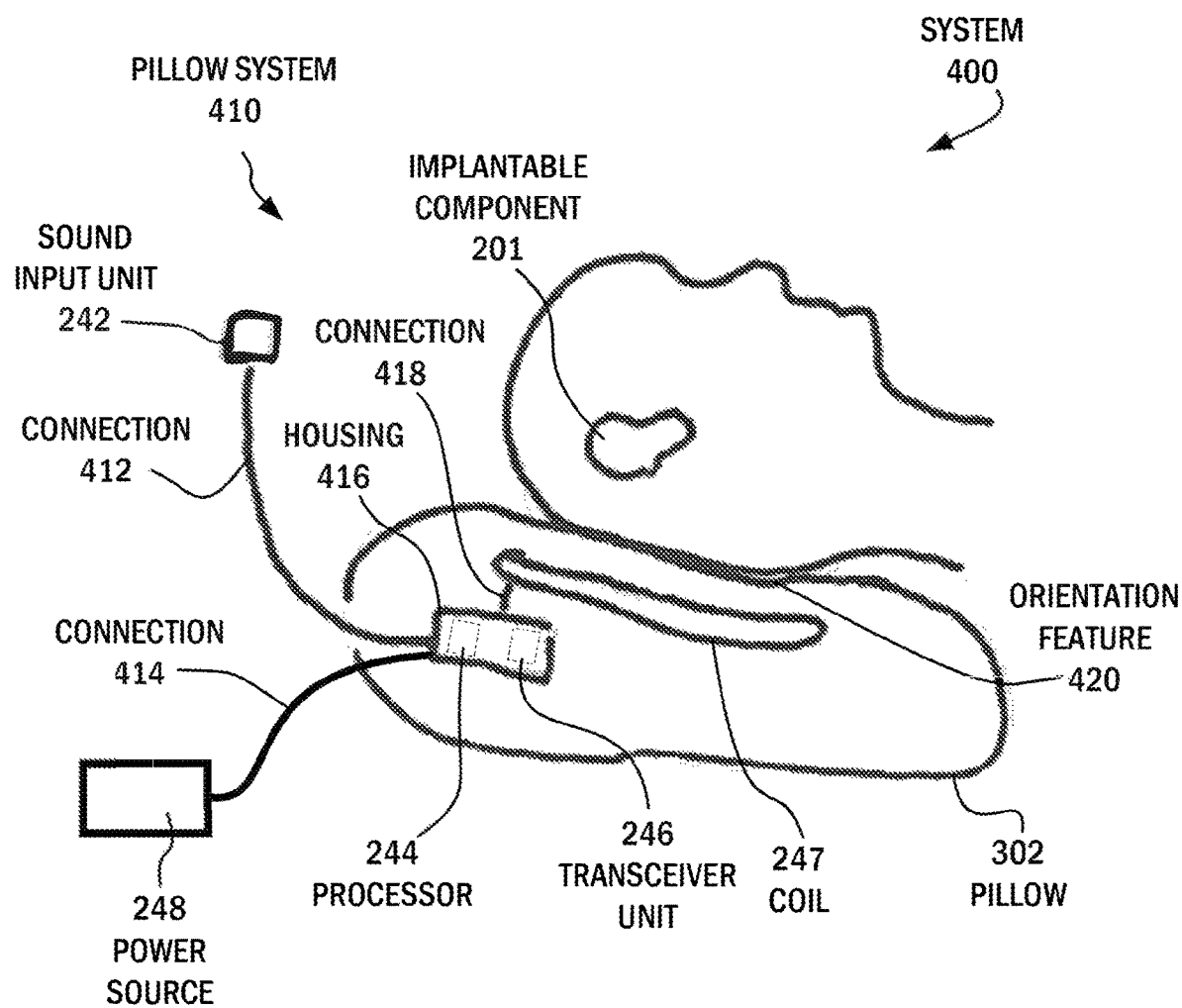
FIG. 4 illustrates an example system that includes an implantable component and a pillow system.

FIG. 4 illustrates an example system 400 including an implantable component 201 and a pillow system 410. The pillow system 410 includes a sound input unit 242, a processor 244, a transceiver unit 246, a coil 247, and a power source 248.

As shown, a recipient's head is resting on the pillow 302, which disposes the implantable component 201 proximate the coil 247. In this configuration, the coil 247 is able to transmit power and/or data to the implantable component. As illustrated, the recipient is not wearing a wearable external device (e.g., external device 150 of FIG. 1). In this manner, the only power used by the implantable component 201 is from the coil 247, which makes the coil 247 the sole power source for the implantable component.

In the illustrated configuration, the sound input unit 242 is external to the pillow 302. This can facilitate placement of the sound input unit 242 in a location where it is better able to obtain sound input than within the pillow, where it can be muffled. In some examples, the sound input unit 242 can include an attachment feature (not shown) to facilitate coupling the sound input unit 242 to a particular location, such as a headboard or a wall. The sound input unit can be coupled to the processor 244 over a wired connection 412, though other configurations are also possible. For example, the sound input unit 242 can be coupled to the pillow sound processor 410 using a wireless connection.

As illustrated, the power source 248 is also external to the pillow 302 and coupled to the processor 244 through a wired connection 414. Though, again, the connection can also be made wirelessly. For example, there can be a wireless power transfer configuration, such that the power source 245 can transfer power to the components within the pillow 302 wirelessly, such as via a power coil disposed proximate the pillow 302 and a compatible power coil within the pillow and coupled to the processor 244 or a battery disposed within the pillow 302.

Where one or more of the connections 412, 414 are wired, they can connect to their respective end points (e.g., the sound input unit 242, power source 248, and housing 416) via a readily-detachable coupling, so if a recipient becomes tangled in the connections 412, 414, the connections become detached from their respective endpoints. Such a configuration can increase the recipient acceptance of the system 410.

The processor 244 and the transceiver unit 246 are illustrated as being disposed within a same housing 416. The housing 416 can be configured to be suitable for placement within a pillow 302 and can be surrounded by or include padding to increase the comfort of a recipient using the pillow 302. In some examples, the housing 416 can include an attachment feature (not shown) to facilitate anchoring the housing 416 (and thus the components within the housing) in a particular region within the pillow 302 and to resist the housing 416 from shifting positions within the pillow 302. The coil 247 is connected to the components within the housing 416 via a connection 418.

The housing 416 can also be configured for placement external to the pillow. For example, a recipient's wearable sound processor can be placed in a bedside docking station that is connected to the coil 247 and power source 248. Engagement with the docking station can automatically cause the sound processor to enter a night mode where, for example, the stimulation signal for the implant is appropriately modified (e.g., sound sensitivity is reduced) and/or the battery is recharged from the external power source 248 while the sound processor continues to operate. The docking station can also include an external sound source (e.g., a remote microphone) to supplement or replace the microphone in the wearable sound processor as needed.

As illustrated, the coil 247 is located near a location where a recipient using the pillow 302 rests his or her head. In some configurations, the pillow 302 can include an orientation feature 420 that encourages a recipient to rest his or her head on the pillow 302 in a particular orientation relative to the coil 247. For example, the orientation feature 420 can be a concavity that encourages a recipient to rest their head in a position, such that the implantable component 201 is relatively closer to the coil 247 (e.g., and thus improving a connection therebetween). Further, the pillow 302 can include an orientation feature 420 that encourages a recipient to place the pillow 302 in a particular orientation. For instance, the coil 247 can be disposed near a top portion of the pillow and the orientation feature 420 can encourage (e.g., be shaped to encourage) a top-up placement of the pillow 302, thus placing the coil 247 closer to an area where a recipient's head would rest.

Figure 5:
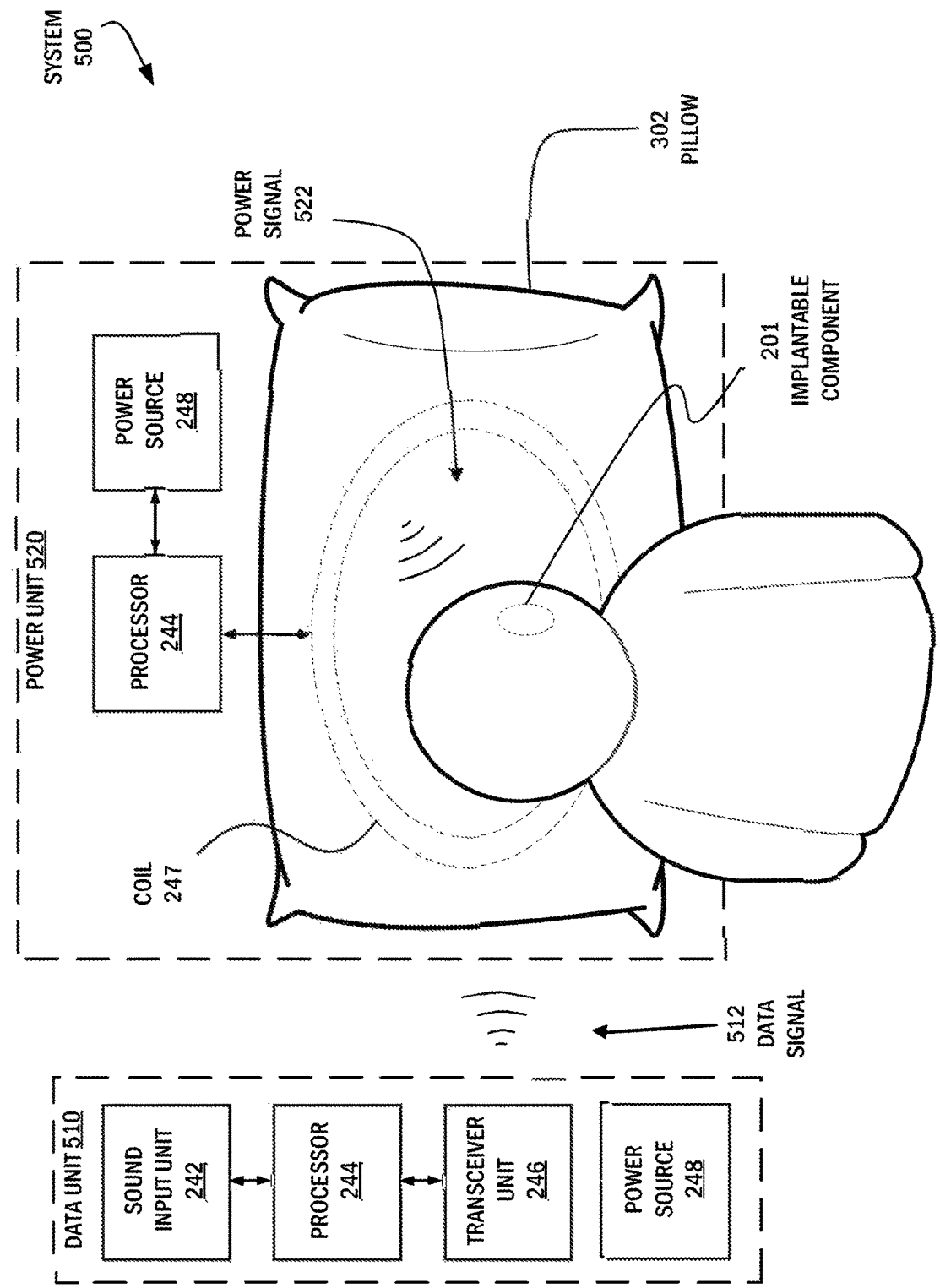
FIG. 5 illustrates an example system having a separate data unit and a separate power unit.

FIG. 5 illustrates an example system 500 having a data unit 510 separate from a power unit 520 (e.g., not sharing any physical components with the power unit 520). The data unit 510 is configured to send data signals 512 to the implantable component 201, and the power unit 520 is configured to send power signals 522 to the implantable component 201.

As illustrated, the data unit 510 includes a sound input unit 242, a processor 244, a transceiver unit 246, and a power source 248. In some examples, the data unit 510 can have one or more components disposed within the pillow 302 and be configured to send a data signal 512 to the implantable component 201 using a coil 247 disposed within the pillow 302. In some examples, the data unit 510 and the power unit 520 can share the coil 247. In other examples, the data unit 510 and the power unit 520 use separate coils disposed within the pillow 302. In some examples, the transceiver unit 246 of the data unit 510 can be configured to send the data signal 512 using a wireless-communication protocol, such as BLUETOOTH (maintained by the BLUETOOTH SPECIAL INTEREST GROUP of Kirkland, Wash.). BLUETOOTH operates using radio waves having frequencies between 2.4 GHz and 2.5 GHz. In this manner, the data unit 510 can be able to communicate with the implantable component 201 across a larger distance than, for example, inductive communication. In some examples, the system 500 can concurrently transmit power and data to the implantable component 201 via distinct communication protocols. For example, the data unit 510 can use a far field protocol (e.g. BLUETOOTH) to communicate (e.g., transmit data) with the implantable component from a location remote from the pillow (e.g., a bedside table or headboard of a bed), and the power unit 520 can use a near field protocol to concurrently communicate (e.g., transmit power) with the implantable component from a location immediately adjacent the recipient's head (e.g., a coil forming part of the pillow).

While the data unit 510 can be a dedicated device, it can be advantageous to allow devices that a recipient uses on a regular basis to operate as the data unit 510. For example, a recipient's mobile phone or a recipient's wearable external medical device (e.g., external device 150) can be configured to operate as the data unit 510. For example, a phone's microphone can operate as the sound input unit 242, the phone's processor can be configured to operate as the processor 244, and a transceiver of the phone can act as the transceiver unit 246 to send a data signal 512 over BLUETOOTH (or another wireless data protocol) to the implantable component 201 based on sound received by the phone's microphone. For instance, there can be an application installed on the phone that configures the phone to operate in this manner.

In another example, a recipient can remove his or her wearable device to go to bed and place the device on a nightstand, in a charging cradle, or elsewhere. While not being worn, the wearable device still includes sound input and processing functionality, though the device can be outside of a functional range for power or data transmission. In some examples, the wearable device can still function as a data transmitter and allow the power unit 520 to take over a power functionality that would otherwise be provided by the wearable device. In some examples, the wearable device is not configured to provide data transmission when not being worn, and an adapter (not shown) can be connected to the wearable device to nonetheless allow it to provide data. For example, the adapter can receive data transmissions from the wearable device and re-transmit the data in a form more suitable for the distance to the implantable component 201.

In some examples, the data unit 510 can be located in another room from the pillow 302 to provide remote-listening functionality. In this manner, the data unit 510 can act as a baby monitor. In some examples, there can be multiple different sound input units 242, which can be placed in different locations and have their output mixed together.

The power unit 520 can be used to provide power to the implantable component 201 via coil 247 disposed in the pillow 302. As illustrated, the processor 244 and the power source 248 of power unit 520 are not disposed within the pillow 302. Instead, only the coil 247 and a connection between the processor 244 and the coil 247 are disposed within the pillow. Arranging the components in this way can increase the comfort of the pillow 302 by reducing the amount of components disposed therein.

The processors 244 and the power sources 248 of the data unit 510 and the power unit 520 can be configured to suit the respective needs of the units. For example, the processor 244 of the data unit 510 may be configured to cause the data signal 512 to be provided and the processor 244 of the power unit 520 may be configured to cause the power signal 522 to be provided by the coil. In a further example, the power unit 520 may require more power to provide its functionality than the data unit 510 does. And the respective power sources 248 may be configured accordingly. For example, the power source 248 of the power unit 520 may be a relatively large battery or a direct current converter/regulator that uses mains power. The power source 248 of the data unit 510 may be, for example, a relatively smaller battery, such as a battery that may be found in an external sound processor. In some examples, the power source 248 of the data unit 510 may nonetheless be connected to mains power for convenience or other reasons.

In some examples, the system 500 can include a hub that is physically separate from the pillow 302 and includes the data unit 510 and the power unit 520. For example, the data unit 510 and the power unit 520 can be combined in a same area or disposed in a same housing. The physically-separate hub can be remote from the pillow 302 but nonetheless electrically connected to, for example, the coil 247 via a wired or wireless connection. The hub can include a power supply for a wireless data transmitter (e.g., data unit 510) and a power supply for a wireless power transmitter (e.g., power unit 520). In some examples, the power supplies can be the same (e.g., a single power source supplies power for both) or separate.

Figure 6:
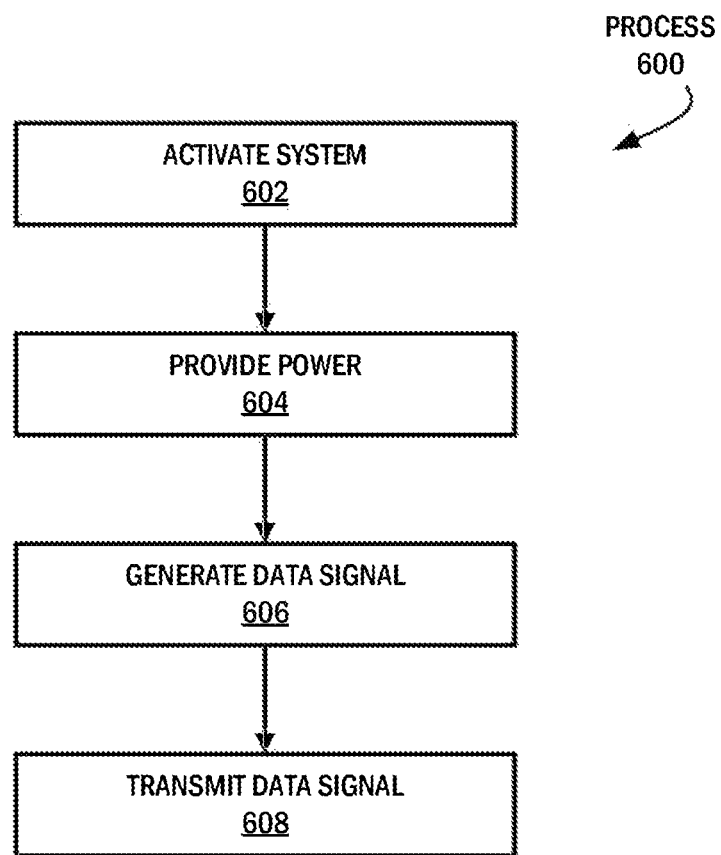
FIG. 6 illustrates an example process for using technology disclosed herein.

FIG. 6 illustrates an example process 600 for using technology disclosed herein with system 500 used as an example. The process 600 can begin with operation 602, which involves activing the system to provide power or data functionality to an implantable component. For example, a recipient can manually activate the system 500 by turning on the components or otherwise causing them to function. In another example, one or both of the data unit 510 and power unit 520 can use their processors 244, transceiver unit 246, and/or coil 247 to automatically interrogate whether there is an implantable component 201 capable of or needing to receive power or data. Following operation 602, the flow of the process 600 can move to operation 604.

Operation 604 involves, responsive to determining that power or data is needed, providing power to the implantable component. For example, the power unit 520 can transfer power to the implantable component 201 using the coil 247. In this manner, the power unit 520 can directly power the implantable component 201 using the power signal. Following operation 604, the flow can move to operation 606.

Operation 606 involves generating a data signal. In the example of system 500, the data unit 510 can obtain output from the sound input unit 242 and generate the data signal 512 based thereon using the processor 244. With the data signal generated, the flow can move to operation 608.

Operation 608 involves transmitting the data signal to the implantable component. For example, the processor 244 can cause a transmitter of the transceiver unit 246 to provide the data signal 512 to the implantable component 201. For example, the data signal 512 can include data encoded and transmitted as part of a BLUETOOTH signal using radio waves having frequencies between 2.3 GHz and 2.5 GHz; 2.4 GHz and 2.5 GHz; or other far field communication protocols and frequencies.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in and described with respect to FIGS. 1 and 2. In general, additional configurations can be used to practice the methods and systems herein and/or some aspects described can be excluded without departing from the methods and systems disclosed herein.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and methods to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

The invention claimed is:

1. A headrest system, comprising:
a headrest structure configured to at least partially receive a head of a recipient of an implantable component of an implantable medical device;
an external coil disposed in the headrest structure;
at least one sound input device integrated in the headrest structure;
at least one power supply; and
a processor disposed on the headrest structure, and wherein the processor is configured to:
determine that the implantable component is in a proximity to the external coil;
provide a signal representative of sound received at the at least one sound input device to an implantable coil of the implantable component; and
responsive to a determination that the implantable component is in the proximity to the external coil, cause the external coil to transfer of operational power from the at least one power supply to the implantable component.

2. The headrest system of claim 1, wherein the external coil is at least two times as large as the implantable coil.

3. The headrest system of claim 1, wherein the headrest structure comprises a pillow and the external coil is integrated within the pillow.

4. The headrest system of claim 1, wherein the processor is configured to modulate the signal representative of the sound with the operational power.

5. The headrest system of claim 1, wherein the at least one sound input device is a microphone coupled to the processor, and wherein the signal representative of the sound comprises sound data obtained from the microphone.

6. The headrest system of claim 1, wherein:
the processor is configured to cause the external coil to continuously provide fluctuating power to the implantable medical device over a period of time.

7. The headrest system of claim 1, wherein the at least one power supply comprises:
a first power supply configured to power the processor separately from the external coil, and
a second power supply configured to power the external coil separately from the processor.

8. The headrest system of claim 1, further comprising:
a wireless power transmitter, and
a wireless data transmitter.

9. The headrest system of claim 8, wherein the headrest system is configured to supply power to the implantable medical device via the wireless power transmitter, and to concurrently supply data to the implantable medical device via the wireless data transmitter.

10. The headrest system of claim 8, wherein the wireless data transmitter is physically separate from the wireless power transmitter.

11. The headrest system of claim 8, further comprising:
a hub that is physically separate from the headrest structure.

12. The headrest system of claim 11, wherein the hub comprises a power supply for the wireless data transmitter separate from the wireless power transmitter, and a separate power supply for the wireless power transmitter separate from the wireless data transmitter.

13. The headrest system of claim 11, wherein the wireless power transmitter is electrically connected to the hub.

14. The headrest system of claim 1, wherein the headrest structure comprises a pillow and a pillow cover at least partially enclosing the pillow, wherein the external coil is at least one of integrated with the pillow cover or disposed between the pillow cover and the pillow.

15. The headrest system of claim 1, wherein the processor is configured to determine the proximity of the implantable coil to the external coil.

16. The headrest system of claim 15, wherein the processor is configured to control the transfer of the operational power from the at least one power supply to the implantable component based on the proximity of the implantable coil to the external coil.

17. The headrest system of claim 1, wherein to control the transfer of the operational power from the at least one power supply to the implantable component based on the proximity of the implantable coil to the external coil comprises selecting between at least two transmission schemes for the transfer of the operational power.

18. The headrest system of claim 17, wherein selecting between the at least two transmission schemes includes selecting between at least near-field electromagnetic radiation and far field electromagnetic radiation.

19. The headrest system of claim 1, wherein the processor is configured to cause the external coil to transfer at least one of the operational power and the signal representative of the sound over far field electromagnetic radiation based on the proximity of the implantable coil to the external coil.

20. The headrest system of claim 1, wherein the signal representative of the sound comprises audio data that is representative of a surrounding sound environment.

\* \* \* \* \*